United States Patent [19]

Engel

[11] 4,368,205
[45] Jan. 11, 1983

[54] 4-HETEROCYCLIC-SUBSTITUTED-2-INDANYL ALCOHOLS AND INSECTICIDAL ESTER DERIVATIVES

[75] Inventor: John F. Engel, Medina, N.Y.

[73] Assignee: FMC Corporation, Philadelphia, Pa.

[21] Appl. No.: 303,292

[22] Filed: Sep. 17, 1981

Related U.S. Application Data

[63] Continuation-in-part of Ser. No. 202,813, Oct. 31, 1980, Pat. No. 4,346,251, which is a continuation-in-part of Ser. No. 42,372, May 24, 1979, Pat. No. 4,263,319.

[51] Int. Cl.³ ............ A01N 43/36; A01N 43/02; C07D 207/12; C07D 333/24
[52] U.S. Cl. .................... 424/274; 424/251; 424/263; 424/270; 424/272; 424/275; 424/285; 549/78; 549/79; 549/497; 544/335; 544/336; 544/224; 546/342; 546/339; 546/203; 546/204; 546/214; 546/235; 546/239; 546/247; 548/562
[58] Field of Search ............... 424/251, 263, 270, 272, 424/274, 275, 285; 260/326.5 C; 549/78, 79, 497; 544/335, 336, 224; 546/342, 339; 548/203, 204, 214, 235, 239, 247

[56] References Cited

U.S. PATENT DOCUMENTS

| | | | |
|---|---|---|---|
| 3,647,857 | 3/1972 | Morgan | 560/124 |
| 3,663,677 | 5/1972 | Juby et al. | 568/808 |
| 3,923,866 | 12/1975 | Sans et al. | 568/808 |
| 4,024,163 | 5/1977 | Elliott et al. | 260/347.4 |
| 4,157,397 | 6/1979 | Engel | 424/274 |
| 4,160,842 | 7/1979 | Engel | 424/274 |
| 4,183,948 | 1/1980 | Huff | 424/304 |
| 4,263,319 | 4/1981 | Engel | 560/105 |
| 4,346,251 | 8/1982 | Engel | 568/808 |

Primary Examiner—Alan Siegel
Attorney, Agent, or Firm—Robert M. Kennedy; H. Robinson Ertelt; Robert L. Andersen

[57] ABSTRACT

Disclosed are novel compounds of the formula

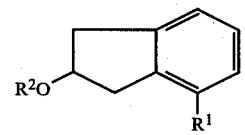

wherein $R^1$ is a heterocyclic radical selected from furanyl, thienyl, pyridyl, pyrimidyl, oxazolyl, pyrrolyl, isoxazolyl, thiazolyl, and isothiazolyl, and $R^2$ is hydrogen, a tetramethylcylopropanecarbonyl group, a 1-(substituted-phenyl)-2-methylpropyl-1-carbonyl group, a 1-(4-ethoxyphenyl)-2-dichlorocyclopropanecarbonyl group, or a substituted-vinyl-cyclopropanecarbonyl group. The compounds wherein $R^2$ is other than hydrogen are insecticides.

13 Claims, No Drawings

4-HETEROCYCLIC-SUBSTITUTED-2-INDANYL ALCOHOLS AND INSECTICIDAL ESTER DERIVATIVES

The present application is a continuation-in-part of U.S. Ser. No. 202,813, filed Oct. 31, 1980 issued Aug. 24, 1982 as U.S. Pat. No. 4,346,251, which is a continuation-in-part of U.S. Ser. No. 042,372, filed May 24, 1979, issued Apr. 21, 1981 as U.S. Pat. No. 4,263,319, the disclosures of both of which are incorporated herein by reference.

The application is directed to a novel alcohol for use in preparing cyclopropanecarboxylate and related insecticides, to insecticides employing this alcohol, and to an insecticidal method and composition. More particularly, the invention is directed to a 4-heterocyclic-substituted-2-indanol and its insecticidal ester derivatives.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxyphenylmethyl alcohol (see *Synthetic Pyrethroids*, ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenylmethyl 3-(2,2-dichloroethenyl)-2,2-dimethylcyclopropanecarboxylate, exemplifies use of both newer acid and alcohol moieties in a single compound.

The present invention provides a novel indanyl alcohol and certain ester derivatives thereof which have a high level of insecticidal activity.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with 1 or more halogen atoms. The term "insecticide" is used in its broadest sense, and includes compounds possessing activity against true insects, acarids, and other household veterinary or crop pests of the phylum Arthropoda. These definitions are applicable throughout the specification and claims except where a contrary meaning is clearly indicated.

The novel compounds of this invention have the general formula

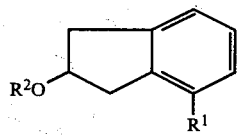

in which $R^1$ is a phenyl, phenoxy, phenylthio, benzyl or heterocyclic radical which may be substituted with halogen, lower alkyl, halo(lower)alkyl, lower alkoxy, lower alkylthio, cyano or nitro, particularly halogen or lower alkyl. The heterocyclic radical is advantageously a 5 or 6 membered ring consisting of carbon and 1 to 3 ring members selected from oxygen, nitrogen, and sulfur. Suitable heterocyclic radicals include furanyl, thienyl, pyridyl, pyrimidyl, oxazolyl, pyrrolyl, isoxazolyl, thiazolyl, and isothiazolyl, the thienyl and pyrrolyl radicals, especially 2-thienyl and 1-pyrrolyl, being of particular interest. $R^2$ is hydrogen; 2,2,3,3-tetramethylcyclopropanecarbonyl; 1-(substituted-phenyl)-2-methylpropyl-1-carbonyl, particularly 1-(4-chlorophenyl)-2-methylpropyl-1-carbonyl; 1-(4-ethoxyphenyl)-2,2-dichlorocyclopropanecarbonyl; or a group of the formula:

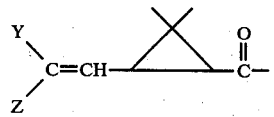

wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen. The novel alcohols are the compounds in which $R^2$ is hydrogen whereas in the insecticidal compounds $R^2$ is other than hydrogen.

Particularly useful insecticides of the present invention are the cyclopropanecarboxylates in which one of Y and Z is halogen, such as chlorine or bromine, and the other, the same or different, is halogen or a perhaloalkyl group such as trihalomethyl, particularly trifluoromethyl, and $R^1$ is phenyl. These compounds are described in greater detail in the parent cases of the present application. The insecticidal compounds wherein $R^1$ is a heterocyclic radical such as furanyl, thienyl, pyridyl, pyrimidyl, oxazolyl, pyrrolyl, isoxazolyl, thiazolyl, or isothiazolyl, particularly thienyl or pyrrolyl, more particularly 2-thienyl or 1-pyrrolyl, and Y and Z are as just described constitute a second preferred subgenus, and, along with the corresponding alcohol intermediates, are of prime interest with respect to the present application.

The cyclopropanecarboxylates having the acid residue of formula II have cis and trans isomeric forms, i.e., the carboxy and the substituted vinyl groups at the 1 and 3 positions of the cyclopropane ring are either cis or trans with respect to each other. Preparation of these compounds will usually yield a mixture of the cis and trans isomers, designated herein as cis,trans, in which the ratio of cis to trans may vary over a wide range. For purposes of this application the designations cis and trans are assigned in accordance with P. E. Burt, et al., *Pestic. Sci.*, 5 791–799 (1974). The compounds where Y is different from Z may also exist as E or Z isomers or as mixtures of E and Z isomers, designated E,Z, depending upon the spatial relationship of substituents on the α-carbon of the vinyl group to those on the β-carbon of the vinyl group. The alcohols or alcohol moiety of the insecticidal esters of the present invention may have either the 2R or the 2S absolute configuration, or the compound may be comprised of a mixture of the isomers.

In the cyclopropanecarboxylate art it is known there may be substantial differences in the level of insecticidal activity of the cis and trans isomers. In general, as between the cis and trans isomer of a given cyclopropanecarboxylate, the cis isomer is usually more active than the trans and also more active than the cis,-trans mixture. Similarly, differences in activity may also occur with respect to the E and Z isomers, and with respect to the R and S isomers of the alcohol moiety.

The present invention includes within its scope any of the compounds of formula I having the cis or trans or cis,trans acid moiety, the E or Z or E,Z acid moiety, or the 2R or 2S or 2R,S alcohol moiety.

The alcohols of this invention may be prepared by various methods including the methods outlined in the schemata below for 4-(2-thienyl)-2-indanol and 4-(1-pyrrolyl)-2-indanol. The pyrrolylindanol was prepared by two different methods, each of which is shown below (schema 2 and 3) and described in greater detail in the examples (Examples 2 and 3). Preparation of the thienylindanol is more fully described in Example 1.

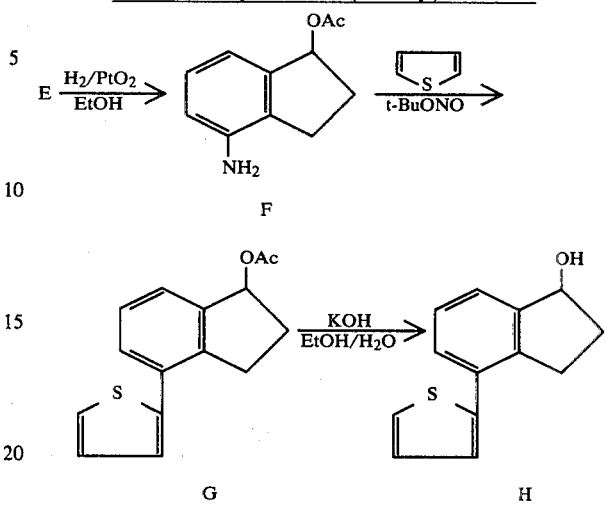
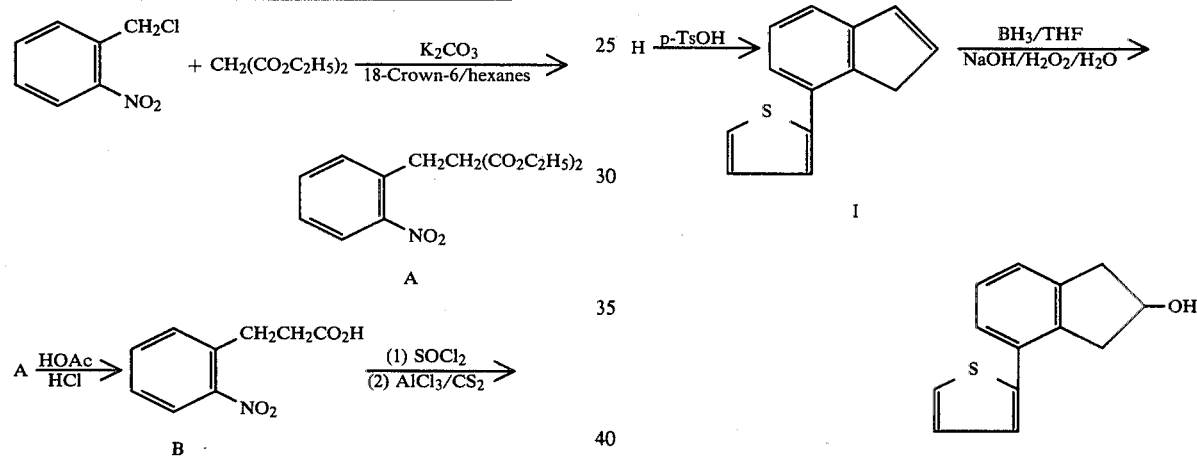
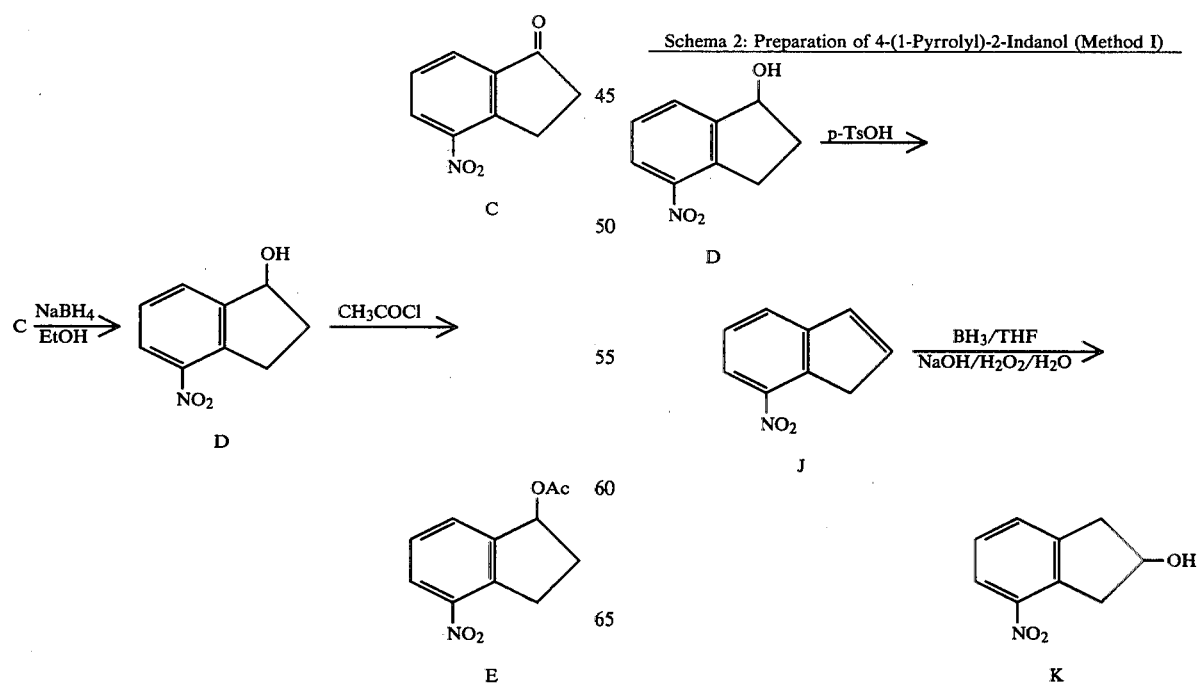

-continued
Schema 2: Preparation of 4-(1-Pyrrolyl)-2-Indanol (Method I)

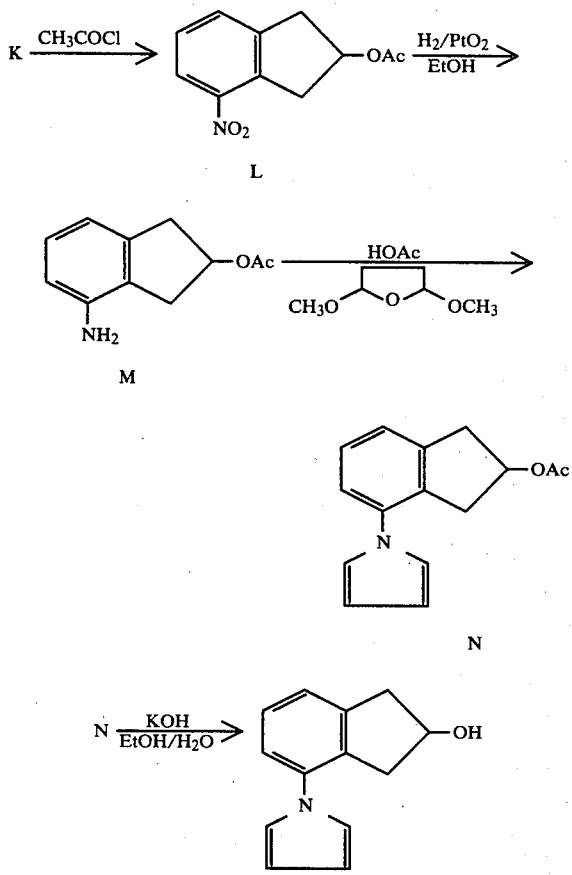

Schema 3: Preparation of 4-(1-Pyrrolyl)-2-Indanol (Method II)

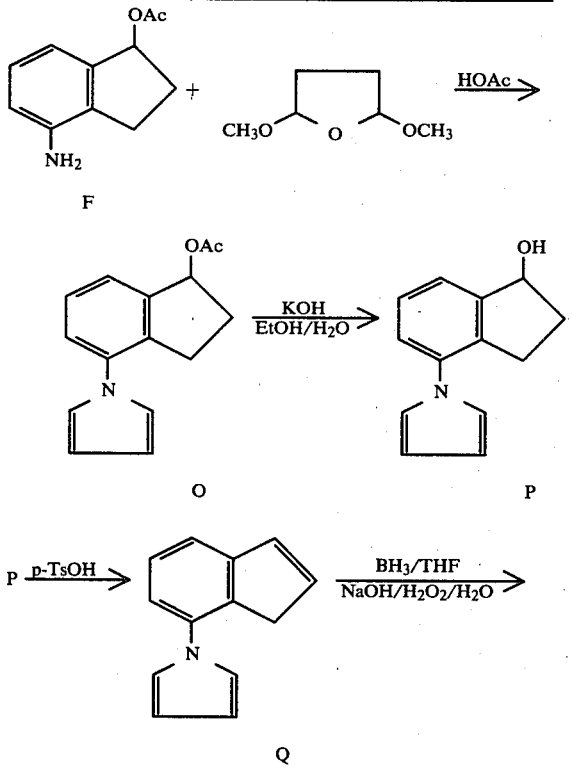

-continued
Schema 3: Preparation of 4-(1-Pyrrolyl)-2-Indanol (Method II)

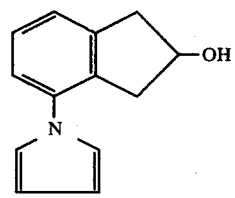

The hydroboration steps in the schemata above produce a 4-substituted-1-indanol as a side product in addition to the desired 2-indanol. The 2-indanol may be effectively purified by subjecting the mixture to dehydration conditions to decompose the more labile 1-indanol, followed by separation of the desired 2-indanol by chromatography. This procedure is described in detail in step J of Example 1.

Many of the intermediate acids from which the insecticidal esters of this invention are prepared are well known, and may be produced by methods in the literature of the art. Those acids not disclosed in the prior art may be prepared by analogous methods. Tetramethylcyclopropanecarboxylic acid and 1-(4-chlorophenyl)-2-methylpropyl-1-carboxylic acid may be prepared by the methods outlined in *Synthetic Pyrethroids*, ACS Symposium Series, No. 42, M. Elliott, Ed., American Chemical Society, Washington, D.C., 1977, chapter 4, FIG. 4, page 48 and accompanying text; 1-(4-ethoxyphenyl)-2,2-dichlorocyclopropanecarboxylic acid may be prepared by the method of Holan and Walser, U.S. Pat. No. 4,220,591; dihaloethenylcyclopropanecarboxylic acids, acids having the acyl group of formula II wherein each of Y and Z is a halogen atom, may be prepared by the method of Elliott et al., U.S. Pat. No. 4,024,163; and (perhaloalkyl)ethenylcyclopropanecarboxylic acids, acids having the acyl group of formula II in which one of Y and Z is halogen and the other is a perhaloalkyl group, may be prepared by the method disclosed by Engel, U.S. Pat. No. 4,238,505. The pertinent disclosures of the above four references are incorporated herein by reference.

The insecticidal compounds having the acid residue of formula II may be prepared, as exemplified below, from alkanoates of the formula

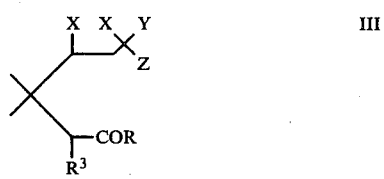

in which Y and Z are defined as above; R is lower alkoxy, such as methoxy or ethoxy, or a 4-heterocyclic-substituted-2-indanyloxy moiety from an alcohol of formula I; $R^3$ is hydrogen, lower alkylcarbonyl, lower alkoxycarbonyl, or cyano, preferably hydrogen; and X is chloro or bromo. Example 4 illustrates a method for preparation of the alkanoate intermediates of Formula III whereby a lower alkyl 3,3-dimethyl-4-pentenoate is allowed to react with a compound of the formula $X_2C(Y)(Z)$ wherein X, Y, and Z are as defined above.

Dehydrohalogenation of the compound of formula III followed, if necessary, by hydrolysis of the ester and, also if necessary, halogenation of the resulting carboxyl group gives a compound of the formula

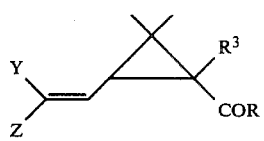

in which R is lower alkoxy, hydroxy, halogen, or a 4-heterocyclic-substituted-2-indanyloxy moiety from an alcohol of formula I, and Y, Z and $R^3$ are as defined above. The dehydrohalogenation reaction may proceed through one or more intermediates of the formulas:

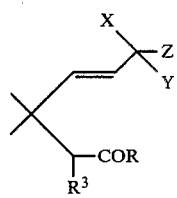

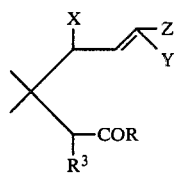

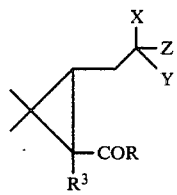

and may be conducted in a single step by elimination of 2 equivalents of hydrogen halide, HX, to give a compound of formula IV directly, or in multiple steps under conditions allowing a sequential elimination of the 2 equivalents of HX in separate reactions. These intermediates or mixtures thereof may be recovered if desired. The compound of formula IV is then converted to the ester of formula I by methods known to the art, for example, by removing $R^3$ (if other than hydrogen) and, where R is lower alkoxy, hydroxy, or halogen, esterifying or transesterifying with a 4-heterocyclic-substituted-2-indanol of formula I ($R^2$ is hydrogen).

The examples which follow illustrate preparation of the insecticidal compounds and novel intermediates therefor in accordance with the general methods described above. In the examples all temperatures are in degrees Celsius, all pressures are in mm Hg, and reduced pressure for concentrations of liquid was produced by a water aspirator unless otherwise specified.

Examples 1-3 illustrate the preparation of compounds of formula I wherein $R^2$ is hydrogen.

EXAMPLE 1

Synthesis of 4-(2-Thienyl)-2-Indanol

A. Preparation of diethyl (2-nitrophenylmethyl)-1,3-propanedioate (Compound A, Schema 1)

A stirred mixture of 100.0 g (0.583 mole) of 2-nitrophenylmethyl chloride, 91.2 g (0.570 mole) of diethylmalonate, 80.4 g (0.583 mole) of potassium carbonate, and 1.5 g (0.006 mole) of 1,4,7,10,13,16-hexaoxacyclooctadecane in 175 mL of hexane was heated under reflux for 30 hours. The reaction mixture was cooled to ambient temperature, and was extracted with 500 mL of water. The two phases were separated and the aqueous layer washed with toluene. The organic phase was combined with the toluene wash, and was dried with sodium sulfate. The mixture was filtered, and the filtrate concentrated under reduced pressure to give 164.2 g of a residual oil. Gas chromatographic analysis of the oil showed it to contain 51.2% diethyl (2-nitrophenylmethyl)-1,3-propanedioate.

The nmr spectrum was consistent with the assigned structure.

B. Preparation of 3-(2-nitrophenyl)propionic acid (Compound B, Schema 1)

The 164.2 g of oil containing diethyl (2-nitrophenylmethyl)-1,3-propanedioate, from Step A, was combined with 1 L of acetic acid and 1 L of aqueous 20% hydrochloric acid, and heated under reflux for 16 hours. The reaction mixture was cooled to ambient temperature, and concentrated under reduced pressure to give a residue. The residue was stirred with 450 mL of water, then 450 mL of aqueous 10% sodium hydroxide solution was added. The mixture was stirred for one hour, then was extracted with four portions of 450 mL each of diethyl ether. The organic layer was discarded. The aqueous layer was acidified with hydrochloric acid, and extracted with three portions of 300 mL each of diethyl ether. The combined extracts were dried with sodium sulfate, filtered, and the filtrate concentrated under reduced pressure to give a solid residue. The solid was dissolved with heating in 200 mL of toluene, and the solution was stirred for 16 hours while cooling to ambient temperature. The resultant slurry was further cooled to 10° C., and the solid collected by filtration. The solid was washed with pentane to give 74.2 g of 3-(2-nitrophenyl)propionic acid, m.p. 111°–112° C.

C. Preparation of 4-nitro-1-indanone (Compound C, Schema 1)

A stirred solution of 74.2 g (0.38 mole) of 3-(2-nitrophenyl)propionic acid and 53.6 g (0.45 mole) of thionyl chloride in 250 mL of methylene chloride was heated under reflux for 16 hours. The reaction mixture was concentrated under reduced pressure to give a residue, which was dissolved in 100 mL of methylene chloride. The solution was concentrated under reduced pressure, and the residue was subjected to high vacuum to give 3-(2-nitrophenyl)propionyl chloride as an oil.

A stirred mixture of 64.1 g (0.48 mole) of aluminum chloride and 300 mL of carbon disulfide was cooled to 5° C., and a solution of the nitrophenylpropionyl chloride from above in 100 mL of carbon disulfide was added dropwise. During the addition the temperature of the reaction mixture was maintained at 5°–10° C. Upon complete addition, the reaction mixture was stirred at 5°

C. for 0.25 hours, at ambient temperature for 0.5 hour, then under reflux for 3.5 hours, and finally at ambient temperature for 16 hours. The reaction mixture was poured into 100 mL of ice-water, and the mixture was stirred for one hour and extracted with four portions of 400 mL each of diethyl ether. The combined ether extracts were dried over sodium sulfate, filtered, and the filtrate concentrated under reduced pressure to give a solid residue. The residue was crystallized from ethanol after treatment with decolorizing carbon to give, in two fractions, 39.8 g of 4-nitro-1-indanone, m.p. 94°–97° C.

The nmr spectrum was consistent with the assigned structure.

D. Preparation of 4-nitro-1-indanol (Compound D, Schema 1)

To a stirred suspension of 126 g (0.711 mole) of 4-nitro-1-indanone in 1.25 L of ethanol was added portionwise 15.6 g (0.411 mole) of sodium borohydride. The complete addition required 15 minutes during which the temperature of the reaction mixture rose from 25° C. to 45° C. The reaction mixture was stirred at ambient temperature for 16 hours, then was poured into 3 L of water. The mixture was stirred for 0.5 hour, and extracted with three portions of 300 mL each of methylene chloride. The combined extracts were dried over magnesium sulfate, filtered, and the filtrate concentrated under reduced pressure to give an oily residue. The residue was digested with 27 L of petroleum ether. The solvent was separated by decantation, and was cooled to give a solid precipitate. The solid was collected by filtration and dissolved in 1–2 L of diethyl ether. The solution was treated with 10 g of decolorizing carbon, filtered, and the filtrate concentrated under reduced pressure to give 56.2 g of product. Further treatment of the petroleum ether filtrate from above gave an additional 26.2 g of product. Total yield of 4-nitro-1-indanol was 82.4 g; m.p. 72°–73° C.

E. Preparation of 4-nitro-1-indanyl acetate (Compound E, Schema 1)

A stirred solution of 40.0 g (0.51 mole) of acetyl chloride and 43.9 g (0.56 mole) of pyridine in 100 mL of toluene was cooled to 5° C., and a solution of 83.0 g (0.46 mole) of 4-nitro-1-indanol in 30 mL of toluene was added dropwise. Upon complete addition, the reaction mixture was stirred at 5° C. for 10 minutes, then was allowed to warm to ambient temperature and was stirred for 16 hours. The reaction mixture was filtered, and the filtrate concentrated under reduced pressure to give 102.7 g of 4-nitro-1-indanyl acetate as an oil.

The ir spectrum was consistent with the assigned structure.

F. Preparation of 4-amino-1-indanyl acetate (Compound F, Schema 1)

A solution of 10.0 g (0.045 mole) of 4-nitro-1-indanyl acetate in 200 mL of ethanol was mixed with 0.1 g of platinum oxide in 20 mL of ethanol, and the mixture was contacted with hydrogen in a Parr hydrogenator. Upon complete uptake of hydrogen, the reaction mixture was allowed to stand for 16 hours. The platinum oxide was removed by filtration through diatomaceous earth, and the filter cake was washed with ethanol. The ethanol washings were combined with the filtrate, and the whole was concentrated under reduced pressure to give 8.4 g of 4-amino-1-indanyl acetate as an oil.

The ir spectrum was consistent with the assigned structure.

The reaction was repeated several times. In all, 102.7 g of the 4-nitro compound was converted to the 4-amino derivative. The total yield of 4-amino-1-indanyl acetate was 85.1 g.

G. Preparation of 4-(2-thienyl)-1-indanyl acetate (Compound G, Schema 1)

To a stirred solution of 15.0 g (0.079 mole) of 4-amino-1-indanyl acetate in 100 mL (1.25 moles) of thiophene was added dropwise 18.6 mL (0.157 mole) of tert-butyl nitrite. The addition caused an exothermic reaction, raising the temperature of the reaction mixture to 60° C. Upon complete addition, the reaction mixture was stirred for 1.5 hours while cooling to ambient temperature. The reaction mixture was dissolved in 350 mL of n-heptane, and the solution was dried over magnesium sulfate, filtered through a pad of magnesium sulfate, and the filtrate concentrated under reduced pressure to give an oil residue. The oil was purified by column chromatography on silica gel, eluting with hexane, then with 1% ethyl acetatehexane. The appropriate fractions were combined and concentrated under reduced pressure to give 3.5 g of 4-(2-thienyl)-1-indanyl acetate.

The nmr and ir spectra were consistent with the assigned structure.

H. Preparation of 4-(2-thienyl)-1-indanol (Compound H, Schema 1)

To 3.5 g (0.014 mole) of 4-(2-thienyl)-1-indanyl acetate was added a solution of 1.1 g (0.019 mole) of potassium hydroxide in 19.5 mL of water and 39 mL of ethanol. The reaction mixture was stirred for three hours at 60°–70° C., then for 16 hours at ambient temperature. The reaction mixture was concentrated under reduced pressure to give an oil residue. The oil was slurried in 75 mL of water for one hour, causing the oil to solidify. The solid was washed with water, air dried, then recrystallized from toluene to give, in three crops, 2.4 g of 4-(2-thienyl)-1-indanol, m.p. 101°–103.5° C.

I. Preparation of 7-(2-thienyl)-1H-indene (Compound I, Schema 1)

A stirred solution of 2.4 g (0.011 mole) of 4-(2-thienyl)-1-indanol and 0.15 g of p-toluenesulfonic acid in 60 mL of toluene was heated under reflux, and the theoretical amount of water by-product was collected in a Dean-Stark trap. The reaction mixture was cooled and washed with two portions of 100 mL each of a 5% aqueous solution of sodium bicarbonate, then with two portions of 50 mL each of water. The organic layer was dried over magnesium sulfate, filtered, and the filtrate concentrated under reduced pressure to give 2.1 g of 7-(2-thienyl)-1H-indene as an oil.

The ir spectrum was consistent with the assigned structure.

J. Preparation of 4-(2-thienyl)-2-indanol

A stirred solution of 1.00 g (0.012 mole) of 2,3-dimethyl-2-butene in 15 mL of tetrahydrofuran under a nitrogen atmosphere was cooled to 0° C., and 11.2 mL (0.012 mole) of borane-tetrahydrofuran complex was added dropwise. Upon complete addition, the reaction mixture was stirred at 0° C. for one hour, then 2.1 g (0.011 mole) of 7-(2-thienyl)-1H-indene in 15 mL of tetrahydrofuran was added dropwise. Upon complete addition, the reaction mixture was stirred at 0° C. for 2.5 hours, then at ambient temperature for 2 hours. The reaction mixture was recooled to 0° C., and 2.04 mL of water, 6.2 mL of 3 N sodium hydroxide, then 6.2 mL of 30% hydrogen peroxide were cautiously added dropwise. Upon complete addition, the reaction mixture was allowed to warm to ambient temperature, then was poured into 100 mL of water. The mixture was extracted with three portions of 75 mL each of diethyl ether. The combined extracts were washed with two portions of 50 mL each of water. The organic layer was dried over magnesium sulfate, filtered, and the filtrate concentrated under reduced pressure to give a residual oil. Gas chromatographic analysis of the oil showed it to be a mixture of the desired 2-indanol and the 1-indanol side product.

The oil was dissolved in 100 mL of toluene, and 0.1 g of p-toluenesulfonic acid was added. The mixture was heated under reflux for 0.5 hour, and by-product water (from dehydration of the 1-indanol) was collected in a Dean-Stark trap. Gas chromatographic analysis of the mixture showed it contained a mixture comprised of 85.7% of the 2-indanol and 14.3% of 7-(2-thienyl)-1H-indene. The reaction mixture was washed with two portions of 100 mL each of a 5% aqueous solution of sodium bicarbonate, then with 100 mL of water. The organic layer was dried over sodium sulfate, filtered, and the filtrate concentrated under reduced pressure to give an oil residue. The oil was subjected to column chromatography on silica gel, eluting with 100% hexane, then with 100% toluene. The appropriate fractions were combined and concentrated under reduced pressure to give 1.1 g of 4-(2-thienyl)-2-indanol.

The nmr spectrum was consistent with the assigned structure.

EXAMPLE 2

Synthesis of 4-(1-Pyrrolyl)-2-Indanol (Method I)

A. Preparation of 7-nitro-1H-indene (Compound J, Schema 2)

In the manner of Example 1, step I, 14.0 g (0.078 mole) of 4-nitro-1-indanol (compound D, schema 1, prepared as in Example 1, step D) was heated in the presence of 0.1 g of p-toluenesulfonic acid and 200 mL of toluene to give 5.6 g of 7-nitro-1H-indene.

B. Preparation of 4-nitro-2-indanol (Compound K, Schema 2)

In the manner of Example 1, step J, hydroboration of 5.6 g (0.035 mole) of 7-nitro-1H-indene in the presence of 3.2 g (0.038 mole) of 2,3-dimethyl-2-butene, 38 mL (0.38 mole) of borane-tetrahydrofuran complex, 7 mL of water, 21 mL of 3 N sodium hydroxide, 21 mL of 30% hydrogen peroxide, and 70 mL of tetrahydrofuran gave 5.3 g of an oil which was shown by gas chromatographic analysis to contain about 60% of the desired 4-nitro-2-indanol. The product was used in the following step without further purification.

C. Preparation of 4-nitro-2-indanyl acetate (Compound L, Schema 2)

In the manner of Example 1, step E, the 5.3 g of product from step B of this Example was treated with 1.8 g (0.023 mole) of acetyl chloride in the presence of 2.0 g (0.025 mole) of pyridine and 25 mL of toluene to give, after column chromatography of crude product on silica gel, 1.8 g of 4-nitro-2-indanyl acetate.

D. Preparation of 4-amino-2-indanyl acetate (Compound M, Schema 2)

In the manner of Example 1, step F, hydrogenation of 2.5 g (0.011 mole) of 4-nitro-2-indanyl acetate in the presence of 0.1 g of platinum oxide and 125 mL of ethanol gave 2.2 g of 4-amino-2-indanyl acetate as a solid.

E. Preparation of 4-(1-pyrrolyl)-2-indanyl acetate (Compound N, Schema 2)

A stirred solution of 0.70 g (0.004 mole) of 4-amino-2-indanyl acetate and 0.56 g (0.004 mole) of 2,5-dimethoxytetrahydrofuran in 1.5 mL of acetic acid was heated under reflux for 3 hours. The reaction mixture was cooled to ambient temperature and poured into 30 mL of chloroform. The mixture was stirred with 30 mL of an aqueous saturated solution of sodium chloride. The organic layer was removed, and the aqueous layer extracted with two portions of 30 mL each of chloroform. The combined organic phases were washed with two portions of 30 mL each of an aqueous saturated solution of sodium chloride. The organic layer was dried over potassium carbonate, filtered, and the filtrate concentrated under reduced pressure to give 0.89 g of 4-(1-pyrrolyl)-2-indanyl acetate.

The nmr and ir spectra were consistent with the assigned structure.

F. Preparation of 4-(1-pyrrolyl)-2-indanol

In the manner of Example 1, step H, hydrolysis of 0.84 g (0.004 mole) of 4-(1-pyrrolyl)-2-indanyl acetate with 0.28 g (0.005 mole) of potassium hydroxide in 5 mL of water and 10 mL of ethanol gave 0.42 g of 4-(1-pyrrolyl)-2-indanol.

The ir spectrum was consistent with the assigned structure.

EXAMPLE 3

Synthesis of 4-(1-Pyrrolyl)-2-Indanol (Method II)

A. Preparation of 4-(1-pyrrolyl)-1-indanyl acetate (Compound O, Schema 3)

A stirred solution of 10.0 g (0.052 mole) of 4-amino-1-indanyl acetate (prepared as in Example 1, step F) and 7.5 g (0.056 mole) of 2,5-dimethoxytetrahydrofuran in 21.2 mL of acetic acid was heated under reflux for 3.5 hours. The reaction mixture was then allowed to cool to ambient temperature, and was stirred for 16 hours. The reaction mixture was poured into 200 mL of chloroform. An aqueous saturated solution of sodium chloride (200 mL) was added, and the mixture was stirred for 10 minutes. The aqueous layer was separated and washed with 50 mL of chloroform. The combined organic phases were washed with two portions of 50 mL each of an aqueous saturated solution of sodium chloride. The organic layer was dried over potassium carbonate, filtered, and the filtrate concentrated under reduced pressure to give 13.2 g of 4-(1-pyrrolyl)-1-indanyl acetate.

The ir spectrum was consistent with the assigned structure.

B. Preparation of 4-(1-pyrrolyl)-1-indanol (Compound P, Schema 3)

In the manner of Example 1, step H, hydrolysis of 13.0 g (0.054 mole) of 4-(1-pyrrolyl)-1-indanyl acetate with 4.3 g of potassium hydroxide in 77 mL of water and 154 mL of ethanol gave 2.9 g of 4-(1-pyrrolyl)-1-indanol, m.p. 80°–81° C.

The nmr and ir spectra were consistent with the assigned structure.

Analysis calc'd for $C_{13}H_{13}NO$: C, 78.35; H, 6.57; Found: C, 79.29; H, 6.74.

C. Preparation of 7-(1-pyrrolyl)-1H-indene (Compound Q, Schema 3)

In the manner of Example 1, step I, heating 2.3 g (0.011 mole) of 4-(1-pyrrolyl)-1-indanol in the presence of 0.1 g of p-toluenesulfonic acid and 50 mL of toluene gave 2.0 g of 7-(1-pyrrolyl)-1H-indene as an oil.

The ir spectrum was consistent with the assigned structure.

D. Preparation of 4-(1-pyrrolyl)-2-indanol

In the manner of Example 1, step J, hydroboration of 2.0 g (0.011 mole) of 7-(1-pyrrolyl)-1H-indene in the presence of 1.0 g (0.012 mole) of 2,3-dimethyl-2-butene, 12 mL (0.012 mole) of borane-tetrahydrofuran complex, 2.1 mL of water, 6.3 mL of 3 N sodium hydroxide, and 6.3 mL of 30% hydrogen peroxide gave a mixture of the desired 2-indanol and 1-indanol side-product as an oil.

The oily mixture was heated with 0.1 g of p-toluenesulfonic acid in 50 mL of toluene for 15 minutes, and by-product water (from dehydration of the 1-indanol) was collected in a Dean-Stark trap. The solution was cooled to room temperature and washed with two portions of 50 mL each of a 5% aqueous solution of sodium bicarbonate then with two portions of 50 mL each of water. The organic layer was dried over sodium sulfate, filtered, and the filtrate concentrated under reduced pressure to give 1.4 g of product as an oil. Gas chromatographic analysis of the oil showed it contained 79% of 4-(1-pyrrolyl)-2-indanol and 14% of 7-(1-pyrrolyl)-1H-indene. The product was used in a subsequent reaction (Example 14) without further purification.

Example 4 illustrates preparation of compounds of Formula III.

EXAMPLE 4

Synthesis of Ethyl 3,3-Dimethyl-4,6,6-Trichloro-7,7,7-Trifluoroheptanoate

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 mL of tertiary butyl alcohol, under a nitrogen atmosphere, was heated at reflux for 16 hours. The reaction mixture was cooled to ambient temperature and extracted with three portions of 100 mL each of diethyl ether. A precipitate formed in the extracts, and was removed by vacuum filtration. The filter cake was washed with two portions of 25 mL each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm.

The nmr spectrum was consistent with the assigned structure.

Examples 5 and 6 illustrate preparation of the lower alkyl esters of formula IV. Example 5 is a two-step process via the intermediate of formula VII. Example 6 is a one-step process.

EXAMPLE 5

Synthesis of Methyl Cis,Trans-3-(2-Chloro-3,3,3-Trifluoro-1-Propenyl)-2,2-Dimethylcyclopropanecarboxylate A. Preparation of methyl cis,trans-3-(2,2-dichloro-3,3,3-trifluoropropyl)-2,2-dimethylcyclopropanecarboxylate A stirred solution of 37.0 g (0.112 mole) of methyl 3,3-dimethyl-4,6,6-trichloro-7,7,7-trifluoroheptanoate, 50 mL of tert-butyl alcohol, 50 mL of dimethylformamide, and 50 mL of hexane, under an argon atmosphere, was cooled to −5° C. To the stirred solution was added dropwise a solution of 16.4 g (0.14 mole) of potassium tert-butoxide in 200 mL of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 g of ammonium chloride in 250 mL of water. The mixture was extracted with two portions of 200 mL each of diethyl ether. The combined ether extracts were washed with two portions of 200 mL each of water. The ether layer was dried with sodium sulfate and filtered. The filtrate was evaporated under reduced pressure to a residual oil. The oil was distilled under reduced pressure to give 19.8 g of methyl cis,trans-3-(2,2-dichloro-3,3,3-trifluoropropyl)-2,2-dimethylcyclopropanecarboxylate; b.p. 55°–57° C./0.09 mm.

The ir and the nmr spectra were consistent with the proposed structure.

Analysis calc'd for $C_{10}H_{13}Cl_2F_3O_2$: C, 40.98; H, 4.47; Found: C, 41.50; H, 4.41.

B. Preparation of methyl cis,trans-3-(2-chloro-3,3,3-trifluoro-1-propenyl)-2,2-dimethylcyclopropanecarboxylate.

A stirred solution of 30.6 g (0.105 mole) of methyl cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 mL of dimethylformamide was heated at 100° C. for 4 hours. The reaction mixture was cooled and poured into a solution of 37.2 mL of concentrated hydrochloric acid in 300 mL of water. The mixture was extracted with three portions of 200 mL each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl cis,trans 3-(2-chloro-3,3,3-trifluoro-1-propenyl)-2,2-dimethylcyclopropanecarboxylate; b.p. 40°–60° C./0.05 mm.

The ir and the nmr spectra were consistent with the proposed structure. The nmr spectra indicated an 88:12 mixture of cis:trans isomers.

Analysis calc'd for $C_{10}H_{12}ClF_3O_2$: C, 46.80; H, 4.71; Found: C, 46.91; H, 4.79.

EXAMPLE 6

Synthesis of Ethyl Cis,Trans-3-(2-Chloro-3,3,3-Trifluoro-1-Propenyl)-2,2-Dimethylcyclopropanecarboxylate To a stirred solution of 78.3 g (0.228 mole) of ethyl 3,3-dimethyl-4,6,6-trichloro-7,7,7-trifluoroheptanoate in 200 mL of distilled ethanol was added dropwise at ambient temperature 500 mL of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 mL of water, and the mixture was extracted with three portions of 50 mL each of diethyl ether. The combined extracts were dried with sodium sulfate and filtered. The filtrate was evaporated under reduced pressure to give, as a residual oil, 58.5 g of ethyl cis,trans-3-(2-chloro-3,3,3-trifluoro-1-propenyl)-2,2-dimethylcyclopropanecarboxylate. The nmr and the ir spectra were consistent with the assigned structure and indicated the product was a mixture of approximately equal parts of cis and trans isomers.

Examples 7 and 8 illustrate preparation of the individual cis and trans isomers of the free acids of formula IV.

EXAMPLE 7

Synthesis of Trans and Cis,Trans-3-(2-Chloro-3,3,3-Trifluoro-1-Propenyl)-2,2-Dimethylcyclopropanecarboxylic Acid A solution of 16.2 g (0.06 mole) of ethyl cis, trans-3-(2-chloro-3,3,3-trifluoro-1-propenyl)-2,2-dimethylcyclopropanecarboxylate in 94 mL (0.078 mole) of a stock solution containing 3.34 g of sodium hydroxide, 94 mL of ethanol and 6 mL of water was stirred while heating under reflux for a period of 18 hours. The reaction mixture was concentrated under reduced pressure, 25 mL of water was added, and the mixture was acidified to pH1 using 6 N hydrochloric acid. The acidified mixture was extracted with two portions of 50 mL each of diethyl ether. The combined extracts were dried with magnesium sulfate and filtered. The filtrate was evaporated under reduced pressure to give a residue. The residue was heated with 50 mL of hexane. The hot hexane was decanted from a tarry residue and cooled to yield a solid precipitate, which was collected by filtration, then dried to give 3.3 g of solid, m.p. 97°-103° C. Concentration of the mother liquor provided a second fraction of solid weighing 0.8 g, m.p. 96°-103° C. Nmr spectra of the two fractions indicated the solids were each trans-3-(2-chloro-3,3,3-trifluoro-1-propenyl)-2,2-dimethylcyclopropanecarboxylic acid. The mother liquor was evaporated to a residue. The residue was taken up in 50 mL of hexane and the solution cooled in a freezer for 18 hours. A solid precipitate was collected by filtration and dried to give 4.3 g of a solid, m.p. 64°-74° C. An nmr spectrum indicated the solid was a 50/50 mixture of cis and trans isomers of 3-(2-chloro-3,3,3-trifluoro-1-propenyl)-2,2-dimethylcyclopropanecarboxylic acid.

EXAMPLE 8

Synthesis of Cis and Cis,Trans-3-(2-Chloro-3,3,3-Trifluoro-1-Propenyl)-2,2-Dimethylcyclopropanecarboxylic Acid A stirred solution of 90.0 g (0.35 mole) of methyl cis,trans-3-(2-chloro-3,3,3-trifluoro-1-propenyl)-2,2-dimethylcyclopropanecarboxylate (approximately 90% cis, prepared in accordance with Example 5B), 5.4 mL of concentrated sulfuric acid and 13.8 mL of water in 138 mL of acetic acid was heated under reflux for 1 hour. The reaction mixture was cooled and extracted with two portions of 100 mL each of diethyl ether. The combined extracts were dried with sodium sulfate, filtered, and the filtrate concentrated under reduced pressure to a solid residue. The residue was digested with 300 mL of hexane and the hexane solution was decanted from a dark, tarry residue and allowed to cool to ambient temperature. A solid precipitate formed and was collected by filtration to give 42.4 g of cis-3-(2-chloro-3,3,3-trifluoro-1-propenyl)-2,2-dimethylcyclopropanecarboxylic acid, as determined by NMR spectroscopy. A melting point was not determined. The melting point of another sample of cis acid prepared at a different time was 108°-110° C. The filtrate was concentrated and cooled to give 5.1 g of solid, identified by NMR spectroscopy to be a 50:50 mixture of cis,trans-3-(2-chloro-3,3,3-trifluoro-1-propenyl)-2,2-dimethylcyclopropanecarboxylic acid. The filtrate was cooled in dry ice to give an additional 8.1 g of a 50:50 mixture of the cis,trans isomers.

Examples 9 and 10 illustrate preparation of the acid halides of formula IV.

EXAMPLE 9

Synthesis of Trans-3-(2-Chloro-3,3,3-Trifluoro-1-Propenyl)-2,2-Dimethylcyclopropanecarbonyl Chloride To a stirred solution of 4.1 g (0.0173 mole) of trans-3-(2-chloro-3,3,3-trifluoro-1-propenyl)-2,2-dimethylcyclopropanecarboxylic acid in 40 mL of toluene at ambient temperature was added 1.7 g (0.022 mole) of pyridine, then 2.6 g (0.022 mole) of thionyl chloride in 25 mL of toluene. Upon complete addition the reaction mixture was stirred at ambient temperature for 17 hours. The reaction mixture was filtered through diatomaceous earth, and the filtrate was evaporated under reduced pressure to give 3.8 g of trans-3-(2-chloro-3,3,3-trifluoro-1-propenyl)-2,2-dimethylcyclopropanecarbonyl chloride.

The ir spectrum was consistent with the assigned structure.

EXAMPLE 10

Synthesis of Cis-3-(2-Chloro-3,3,3-Trifluoro-1-Propenyl)-2,2-Dimethylcyclopropanecarbonyl Chloride A stirred solution of 10.0 g (0.04 mole) of cis-3-(2-chloro-3,3,3-trifluoro-1-propenyl)-2,2-dimethylcyclopropanecarboxylic acid in 100 mL of toluene was heated to 80° C. To this solution at 80° C. was added dropwise over 10 minutes a solution of 10.5 g (0.08 mole) of oxalyl chloride in 5 mL of toluene, and the whole heated at 80° C. for 26 hours. The toluene and excess oxalyl chloride were removed by distillation to give a residual oil which was distilled under reduced pressure using a Kugelrohr distilling system to give 8.2 g of cis-3-(2-chloro-3,3,3-trifluoro-1-propenyl)-2,2-dimethylcyclopropanecarbonyl chloride; b.p. 85° C./0.09 mm.

The nmr and ir spectra were consistent with the proposed structure.

Examples 11–14 illustrate preparation of compounds of formula I wherein $R^2$ is other than hydrogen.

EXAMPLE 11

Synthesis of 4-(2-Thienyl)-2-Indanyl Cis-3-(2-Chloro-3,3,3-Trifluoro-1-Propenyl)-2,2-Dimethylcyclopropanecarboxylate A stirred solution of 0.54 g (0.003 mole) of 4-(2-thienyl)-2-indanol and 0.25 g (0.003 mole) of pyridine in 15 mL of toluene was cooled to 5° C., and 0.65 g (0.003 mole) of cis-3-(2-chloro-3,3,3-trifluoropropenyl)-2,2-dimethylcyclopropanecarbonyl chloride in 5 mL of toluene was added dropwise. Upon complete addition, the reaction mixture was allowed to warm to ambient temperature where it was stirred for 16 hours. The reaction mixture was filtered, and the filtrate concentrated under reduced pressure to give an oil residue. The oil was subjected to column chromatography on silica gel, eluting with 100% hexane then 1% ethyl acetatehexane. The appropriate fractions were combined and concentrated under reduced pressure to give 0.57 g of 4-(2-thienyl)-2-indanyl cis-3-(2-chloro-3,3,3-trifluoropropenyl)-2,2-dimethylcyclopropanecarboxylate as an oil.

The nmr and ir spectra were consistent with the proposed structure.

Analysis calc'd for $C_{22}H_{20}ClF_3O_2S$: C, 59.93; H, 4.57; Found: C, 60.22; H, 4.66.

EXAMPLE 12

Synthesis of 4-(2-Thienyl)-2-Indanyl Cis-3-(2,2-Dichloroethenyl)-2,2-Dimethylcyclopropanecarboxylate In the manner of Example 11, treatment of 0.57 g (0.003 mole) of cis-3-(2,2-dichloroethenyl)-2,2-dimethylcyclopropanecarbonyl chloride with 0.25 g (0.003 mole) of 4-(2-thienyl)-2-indanol in the presence of 0.25 g (0.003 mole) of pyridine and 20 mL of toluene gave 0.49 g of 4-(2-thienyl)-2-indanyl cis-3-(2,2-dichloroethenyl)-2,2-dimethylcyclopropanecarboxylate as an oil. cis-3-(2,2-Dichloroethenyl)-2,2-dimethylcyclopropanecarboxylic acid, from which the acid chloride starting material above was prepared, may be prepared by known methods such as that described in U.S. Pat. No. 4,024,163, to Elliott et al., May 17, 1977, at column 19, lines 45–61.

The nmr and ir spectra were consistent with the assigned structure.

Analysis calc'd for $C_{21}H_{20}Cl_2O_2S$: C, 61.92; H, 4.95; Found: C, 61.45; H, 5.17.

EXAMPLE 13

Synthesis of 4-(1-Pyrrolyl)-2-Indanyl Cis-3-(2-Chloro-3,3,3-Trifluoro-1-Propenyl)-2,2-Dimethylcyclopropanecarboxylate In the manner of Example 11, treatment of 0.52 g (0.002 mole) of cis-3-(2-chloro-3,3,3-trifluoropropenyl)-2,2-dimethylcyclopropanecarbonyl chloride with 0.40 g (0.002 mole) of 4-(1-pyrrolyl)-2-indanol in the presence of 0.20 g (0.003 mole) of pyridine and 17 mL of toluene gave 0.42 g of 4-(1-pyrrolyl)-2-indanyl cis-3-(2-chloro-3,3,3-trifluoro-1-propenyl)-2,2-dimethylcyclopropanecarboxylate as an oil.

The nmr and ir spectra were consistent with the assigned structure.

Analysis calc'd for $C_{22}H_{20}ClF_3NO_2$: C, 62.33; H, 4.99; Found: C, 62.32; H, 4.96.

EXAMPLE 14

Synthesis of 4-(1-Pyrrolyl)-2-Indanyl Trans-3-(2,2-Dichloroethenyl)-2,2-Dimethylcyclopropanecarboxylate In the manner of Example 11, treatment of 0.76 g (0.003 mole) of trans-3-(2,2-dichloroethenyl)-2,2-dimethylcyclopropanecarbonyl chloride with 0.70 g of 4-(1-pyrrolyl)-2-indanol (79% pure, from Example 3, step D) in the presence of toluene and 0.33 g (0.004 mole) of pyridine gave 0.29 g of 4-(1-pyrrolyl)-2-indanyl trans-3-(2,2-dichloroethenyl)-2,2-dimethylcyclopropanecarboxylate as an oil. trans-3-(2,2-Dichloroethenyl)-2,2-dimethylcyclopropanecarboxylic acid, from which the acid chloride starting material above was prepared, may be prepared by known methods, for example, the method described in U.S. Pat. No. 4,024,163, to Elliott et al., May 17, 1977, at column 19, lines 45–61.

The nmr and ir spectra were consistent with the assigned structure.

Analysis calc'd for $C_{21}H_{21}Cl_2NO_2$: C, 64.62; H, 5.42; Found: C, 67.53; H, 5.40.

In the method aspect of this invention, an effective insecticidal amount of the compound of formula I wherein $R^2$ is other than hydrogen is applied to the locus where insect control is desired, i.e., to the insect itself or to the foliage or seeds of agricultural plants. The compounds are useful for the control of household, veterinary, and crop insects and may be applied as technical material or as formulated product. Typical formulations include compositions of the active ingredient in combination with an agriculturally acceptable carrier or extender, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired used dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active agents including nematacides, insecticides, acaracides, fungicides, plant regulators, herbicides, fertilizers, and the like.

In applying these compounds, whether alone or with other agricultural chemicals, an effective insecticidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The insecticidal compounds of this invention were tested for insecticidal activity as described in Examples 15 and 16 below.

EXAMPLE 15

Foliar Application Test

The test compound was dissolved in 5-10 mL of acetone containing 0.25% octylphenoxypolyethoxyethanol. This solution was dispersed in a solution of 90% water, 9.75% acetone, and 0.25% octylphenoxypolyethoxyethanol to give a solution having 512 ppm (w/w) active ingredient. Aliquots of this solution were diluted with an appropriate amount of water to provide solutions containing various concentrations of active ingredient. Test organisms and techniques were as follows: The activity against Mexican bean beetle (*Epilachna varivestis* Muls.), southern armyworm (*Spodoptera eridania* [Cram.]), and cabbage looper (*Trichoplusia ni* [Hubner] was evaluated by spraying the leaves of pinto bean plants with the test solution and infesting with 3rd instar larvae after the foliage had dried. The activity against the pea aphid (*Acyrthosiphon pisum* [Harris]) was evaluated on broad bean plants the leaves of which were sprayed before infestation with adult aphids. The activity against twospotted spider mites (*Tetranychus urticae* [Koch] was evaluated on pinto bean plants the leaves of which were sprayed with test solution after infestation with adult mites. To prevent escape of the insects from the test site, the complete test plant or the incised leaves were placed in capped paper cups. The tests were transferred to a holding room at 80° C. and 50% relative humidity for an exposure period of 48 hours. At the end of this time the dead and living insects were counted and the percent kill was calculated. Results of these tests are summarized in the table below. Mortality figures in parentheses are from retests.

| Cmpd. of Ex. | Conc. (ppm) | Activity in Foliar Application Test Percent Mortality | | | | |
|---|---|---|---|---|---|---|
| | | PA | SAW | TSM | CL | MBB |
| 11 | 64 | 95 | 100 | 90 | — | 95 |
| | 16 | 80(55) | 100 | 73(100) | 100[(1)] | 70 |
| 12 | 64 | 90 | 100 | 43 | 85 | 100 |
| | 16 | 95(80) | 35 | 0 | 50(75) | 100(75) |
| 13 | 64 | 65(100)[(2)] | 0(100)[(2)] | 0 | — | 0(100) |
| | 16 | 20(85) | 0(90) | 0 | — | 0(50) |
| 14 | 64 | 70 | 100 | 0 | 85 | 65(30) |

| Cmpd. of Ex. | Conc. (ppm) | Activity in Foliar Application Test Percent Mortality | | | | |
|---|---|---|---|---|---|---|
| | | PA | SAW | TSM | CL | MBB |
| | 16 | 25 | 65 | 0 | 35[(3)] | 50(10) |

PA—pea aphid
SAW—southern armyworm
TSM—twospotted spider mite
CL—cabbage looper
MBB—Mexican bean beetle
[(1)]Mortality at 4 ppm
[(2)]Mortality at 32 ppm
[(3)]Mortality at 8 ppm

EXAMPLE 16

Topical Application Test

Two replicates of ten larvae of each test species were employed for each test compound. A 9 cm petri dish lined with a piece of filter paper, and containing a food source, was employed for each replicate. An appropriate amount of a solution of the test compound in acetone was applied to the second or third dorsal thoracic segment of each larva. For example, the 5000 ng/insect application was made by applying to the insect a one microliter droplet of a 5 mg/mL solution of toxicant in acetone. The tests were read twenty-four hours after application of the toxicant solution, and the percent kill and $LD_{50}$ values were determined. The insects employed were southern armyworm (*Spodoptera eridania* [Cram.]), cabbage looper (*Trichoplusia ni* [Hubner]), tobacco budworm (*Heliothis virescens* [Fabricius]), Mexican bean beetle (*Epilachna varivestis* Muls.), and milkweed bug (*Oncopeltus faciatus* [Dallas]). The results of these tests are shown in the table below.

| Compound of Example | Activity in Topical Application Test Insect Species | Percent Mortality at 5000 ng/insect | $LD_{50}$ (ng/insect) |
|---|---|---|---|
| 11 | MBB | 100 | 4.3 |
| | MWB | 100 | 91.7 |
| | SAW | 100 | 60.4 |
| | CL | — | 171.0 |
| | TBW | — | 44.5 |
| 12 | MBB | 100 | 5.6 |
| | MWB | 100 | 99.9 |
| | SAW | 100 | 83.4 |
| | CL | — | 212.0 |
| | TBW | — | 103.0 |
| 13 | MBB | 100 | 29.7 |
| | MWB | 100 | 357.0 |
| | SAW | 100 | 46.0 |
| | CL | — | 81.1 |
| | TBW | — | 33.5 |
| 14 | MBB | 100 | 226.0 |
| | MWB | 75 | 2796.0 |
| | SAW | 100 | 292.0 |
| | CL | — | 1651.0 |
| | TBW | — | 353.0 |

MBB—Mexican bean beetle
MWB—milkweed bug
SAW—southern armyworm
CL—cabbage looper
TBW—tobacco budworm

I claim:
1. A compound of the formula

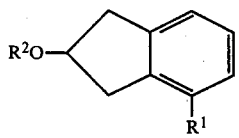

in which $R^1$ is a heterocyclic radical selected from furanyl, thienyl, pyridyl, pyrimidyl, oxazolyl, pyrrolyl, isoxazolyl, thiazolyl, and isothiazolyl, and $R^2$ is 2,2,3,3-tetramethylcyclopropanecarbonyl, 1-(4-chlorophenyl)-2-methylpropyl-1-carbonyl, 1-(4-ethoxyphenyl)-2,2-dichlorocyclopropanecarbonyl, or a group of the formula

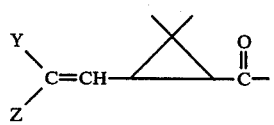

wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen.

2. The compound of claim 1 wherein $R^1$ is thienyl or pyrrolyl.

3. The compound of claim 2 wherein $R^1$ is 2-thienyl or 1-pyrrolyl.

4. The compound of claim 1 wherein $R^2$ is a group of the formula

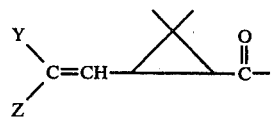

5. The compound of claim 4 wherein one of Y and Z is halogen and the other is halogen or perhaloalkyl, and $R^1$ is 2-thienyl or 1-pyrrolyl.

6. The compound of claim 5 wherein each of Y and Z is halogen.

7. The compound of claim 6 wherein each of Y and Z is a bromine or chlorine atom.

8. The compound of claim 7 wherein each of Y and Z is a chlorine atom.

9. The compound of claim 5 wherein one of Y and Z is halogen and the other is trifluoromethyl.

10. The compound of claim 9 wherein one of Y and Z is a chlorine atom and the other is trifluoromethyl.

11. An insecticidal composition comprising an insecticidally effective amount of the compound of claim 1, 2, 3, 4, 5, 6, 7, 8, 9, or 10.

12. A method for controlling insects which comprises applying to the insect or to a locus where control is desired an insecticidally effective amount of the compound of claim 1, 2, 3, 4, 5, 6, 7, 8, 9, or 10.

13. A method for controlling insects which comprises applying to the insect or to a locus where control is desired an insecticidally effective amount of the composition of claim 11.

* * * * *